United States Patent [19]

Iwasaki et al.

[11] Patent Number: 5,196,316

[45] Date of Patent: Mar. 23, 1993

[54] ENZYME AND DNA CODING THEREFOR

[75] Inventors: Yasuno Iwasaki, Takarazuka; Yoshiki Nishikawa, Kobe, both of Japan

[73] Assignee: Japat Ltd., Basel, Switzerland

[21] Appl. No.: 707,367

[22] Filed: May 30, 1991

[30] Foreign Application Priority Data

Jun. 1, 1990 [JP] Japan ................................ 2-141678
Aug. 10, 1990 [JP] Japan ................................ 2-210535
Nov. 30, 1990 [JP] Japan ................................ 2-329911

[51] Int. Cl.$^5$ .......................... C12D 21/00; C12H 9/00
[52] U.S. Cl. ............................. 435/69.1; 435/68.1; 435/219; 435/232; 530/350; 530/855; 536/23.2
[58] Field of Search .............. 514/2, 8; 530/350, 407, 530/855; 435/68.1, 183, 219, 232, 69.1; 536/27

[56] References Cited

U.S. PATENT DOCUMENTS 4,745,051  5/1988  Smith et al.

FOREIGN PATENT DOCUMENTS 0249412  12/1987  European Pat. Off. ............ 435/212
0308067   3/1989  European Pat. Off. ............ 435/212
0333399   9/1989  European Pat. Off. ............ 435/212

OTHER PUBLICATIONS

Young & Tamburini, Enzymatic Peptidyl α-Amidation Proceeds Through Formation of an α-Hydroxyglycine Intermediate, Mar. 1989, 1933-1934.
Stoffers et al. Proc. Natl. Acad Sci USA 86 735-739 1989.
Bradbury et al., *Nature*, 298:686 (1982).
Eipper et al., PNAS:USA, 80:5144 (1983).
Glembotski et al., *J. Biol. Chem.*, 259:6385 (1984).
Murthy et al., *J. Biol. Chem.*, 261:1815 (1986).
Eipper et al., *Molec. Endocrinol.*, 1:777 (1987).

*Primary Examiner*—Robert A. Wax
*Assistant Examiner*—David Schmickel
*Attorney, Agent, or Firm*—Steven R. Lazar; Shawn P. Foley; W. Murray Spruill

[57] ABSTRACT

The invention concerns a peptidylhydroxyglycine N-C lyase (PHL) catalyzing the reaction $$R\text{-GlyOH} \rightarrow R\text{-NH}_2$$

wherein R represents a peptide residue, and GlyOH represents an α-hydroxyglycine residue linked to the C-terminus of said peptide R by an amide bond, a recombinant DNA molecule coding for a PHL, a method for the preparation of such a recombinant DNA molecule, processes for the preparation of PHL from a natural source or by means of the said recombinant DNA molecule, and the use of PHL for the preparation of an amidated peptide $R\text{-NH}_2$.

11 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 3383 base pairs
      ( B ) TYPE: nucleic acid
      ( C ) STRANDEDNESS: double
      ( D ) TOPOLOGY: linear ( i i ) MOLECULE TYPE: DNA (recombinant)

( v i ) ORIGINAL SOURCE:
      ( A ) ORGANISM: Xenopus laevis
      ( C ) INDIVIDUAL ISOLATE: DNA encoding protein AE-III, precursor to PHL enzyme ( v i i ) IMMEDIATE SOURCE:
  ( B ) CLONE: pAE-III-202-4

( i x ) FEATURE:
  ( A ) NAME/KEY: CDS
  ( B ) LOCATION: 31..2835

( i x ) FEATURE:
  ( A ) NAME/KEY: matpeptide
  ( B ) LOCATION: 1177..2145

( x i ) SEQUENCE DESCRIPTION: SEQ ID NO:1:

```
CTGCAGTAAG GCACAGACCA CAGGGTGGAC ATG GCC AGC CTC AGT AGC AGC TTT        54
                                  Met Ala Ser Leu Ser Ser Ser Phe
                                  -382      -380              -375

CTT GTG CTC TTT CTC TTA TTT CAG AAC AGC TGC TAC TGT TTC AGG AGT        102
Leu Val Leu Phe Leu Leu Phe Gln Asn Ser Cys Tyr Cys Phe Arg Ser
            -370            -365                -360

CCC CTC TCT GTC TTT AAG AGG TAT GAG GAA TCT ACC AGA TCA CTT TCC        150
Pro Leu Ser Val Phe Lys Arg Tyr Glu Glu Ser Thr Arg Ser Leu Ser
        -355                -350                -345

AAT GAC TGC TTG GGA ACC ACG CGG CCC GTT ATG TCT CCA GGC TCA TCA        198
Asn Asp Cys Leu Gly Thr Thr Arg Pro Val Met Ser Pro Gly Ser Ser
    -340                -335                -330

GAT TAT ACT CTA GAT ATC CGC ATG CCA GGA GTA ACT CCG ACA GAG TCG        246
Asp Tyr Thr Leu Asp Ile Arg Met Pro Gly Val Thr Pro Thr Glu Ser
-325                -320                -315

GAC ACA TAT TTG TGC AAG TCT TAC CGG CTG CCA GTG GAT GAT GAA GCC        294
Asp Thr Tyr Leu Cys Lys Ser Tyr Arg Leu Pro Val Asp Asp Glu Ala
-310            -305                -300                -295

TAT GTA GTT GAC TTC AGA CCA CAT GCC AAT ATG GAT ACT GCA CAT CAC        342
Tyr Val Val Asp Phe Arg Pro His Ala Asn Met Asp Thr Ala His His
                -290                -285                -280

ATG CTT CTA TTT GGA TGC AAT ATA CCT TCT TCC ACT GAT GAT TAC TGG        390
Met Leu Leu Phe Gly Cys Asn Ile Pro Ser Ser Thr Asp Asp Tyr Trp
            -275                -270                -265

GAC TGT AGT GCG GGA ACT TGC ATG GAC AAA TCC AGT ATA ATG TAT GCC        438
Asp Cys Ser Ala Gly Thr Cys Met Asp Lys Ser Ser Ile Met Tyr Ala
        -260                -255                -250

TGG GCA AAG AAT GCA CCA CCC ACC AAA CTT CCA GAA GGA GTT GGC TTT        486
Trp Ala Lys Asn Ala Pro Pro Thr Lys Leu Pro Glu Gly Val Gly Phe
    -245                -240                -235

CGT GTT GGA GGG AAA TCA GGC AGT AGA TAT TTT GTG CTT CAA GTT CAC        534
Arg Val Gly Gly Lys Ser Gly Ser Arg Tyr Phe Val Leu Gln Val His
-230                -225                -220                -215

TAT GGA AAT GTG AAA GCA TTC CAG GAT AAA CAT AAA GAT TGC ACG GGG        582
Tyr Gly Asn Val Lys Ala Phe Gln Asp Lys His Lys Asp Cys Thr Gly
                -210                -205                -200

GTG ACA GTA CGA GTA ACA CCT GAA AAA CAA CCG CAA ATT GCA GGC ATT        630
Val Thr Val Arg Val Thr Pro Glu Lys Gln Pro Gln Ile Ala Gly Ile
            -195                -190                -185

TAT CTT TCA ATG TCT GTG GAC ACT GTT ATT CCA CCT GGG GAA GAG GCA        678
Tyr Leu Ser Met Ser Val Asp Thr Val Ile Pro Pro Gly Glu Glu Ala
        -180                -175                -170

GTT AAT TCT GAT ATC GCC TGC CTC TAC AAC AGG CCG ACA ATA CAC CCA        726
Val Asn Ser Asp Ile Ala Cys Leu Tyr Asn Arg Pro Thr Ile His Pro
    -165                -160                -155

TTT GCC TAC AGA GTC CAC ACT CAT CAG TTG GGG CAG GTC GTA AGT GGA        774
Phe Ala Tyr Arg Val His Thr His Gln Leu Gly Gln Val Val Ser Gly
-150            -145                -140                -135

TTT AGA GTG AGA CAT GGC AAG TGG TCT TTA ATT GGT AGA CAA AGC CCA        822
Phe Arg Val Arg His Gly Lys Trp Ser Leu Ile Gly Arg Gln Ser Pro
                -130                -125                -120
```

| | | | | | | | | | | | | | | | | |
|---|---|---|---|---|---|---|---|---|---|---|---|---|---|---|---|---|
| CAG | CTG | CCA | CAG | GCA | TTT | TAC | CCT | GTA | GAG | CAT | CCA | GTA | GAG | ATT | AGC | 870 |
| Gln | Leu | Pro | Gln | Ala | Phe | Tyr | Pro | Val | Glu | His | Pro | Val | Glu | Ile | Ser | |
| | | -115 | | | | | -110 | | | | | -105 | | | | |
| CCT | GGG | GAT | ATT | ATA | GCA | ACC | AGG | TGT | CTG | TTC | ACT | GGT | AAA | GGC | AGG | 918 |
| Pro | Gly | Asp | Ile | Ile | Ala | Thr | Arg | Cys | Leu | Phe | Thr | Gly | Lys | Gly | Arg | |
| | | -100 | | | | -95 | | | | | -90 | | | | | |
| ACG | TCA | GCA | ACA | TAT | ATT | GGG | GGC | ACA | TCT | AAC | GAT | GAA | ATG | TGT | AAT | 966 |
| Thr | Ser | Ala | Thr | Tyr | Ile | Gly | Gly | Thr | Ser | Asn | Asp | Glu | Met | Cys | Asn | |
| | -85 | | | | -80 | | | | | -75 | | | | | | |
| TTA | TAC | ATC | ATG | TAT | TAC | ATG | GAT | GCG | GCC | CAT | GCT | ACG | TCA | TAC | ATG | 1014 |
| Leu | Tyr | Ile | Met | Tyr | Tyr | Met | Asp | Ala | Ala | His | Ala | Thr | Ser | Tyr | Met | |
| -70 | | | | -65 | | | | | -60 | | | | | | -55 | |
| ACC | TGT | GTA | CAG | ACA | GGT | GAA | CCA | AAG | CTA | TTT | CAA | AAC | ATC | CCT | GAG | 1062 |
| Thr | Cys | Val | Gln | Thr | Gly | Glu | Pro | Lys | Leu | Phe | Gln | Asn | Ile | Pro | Glu | |
| | | | | -50 | | | | -45 | | | | | -40 | | | |
| ATT | GCA | AAT | GTT | CCC | ATT | CCT | GTA | AGC | CCT | GAC | ATG | ATG | ATG | ATG | ATG | 1110 |
| Ile | Ala | Asn | Val | Pro | Ile | Pro | Val | Ser | Pro | Asp | Met | Met | Met | Met | Met | |
| | | | -35 | | | | | -30 | | | | | -25 | | | |
| GGA | CAT | GGT | CAC | CAC | CAT | ACA | GAA | GCT | GAG | CCT | GAG | AAG | AAT | ACA | GGA | 1158 |
| Gly | His | Gly | His | His | His | Thr | Glu | Ala | Glu | Pro | Glu | Lys | Asn | Thr | Gly | |
| | | -20 | | | | | -15 | | | | | -10 | | | | |
| CTT | CAG | CAG | CCT | AAA | CGA | GAG | GAG | GAA | GAA | GTA | TTA | GAT | CAG | GAT | GTC | 1206 |
| Leu | Gln | Gln | Pro | Lys | Arg | Glu | Glu | Glu | Glu | Val | Leu | Asp | Gln | Asp | Val | |
| | -5 | | | | | 1 | | | | | 5 | | | | | 10 |
| CAT | TTA | GAG | GAA | GAT | ACA | GAC | TGG | CCG | GGG | GTG | AAC | CTC | AAA | GTG | GGA | 1254 |
| His | Leu | Glu | Glu | Asp | Thr | Asp | Trp | Pro | Gly | Val | Asn | Leu | Lys | Val | Gly | |
| | | | | 15 | | | | | 20 | | | | | 25 | | |
| CAA | GTG | TCA | GGC | TTG | GCT | CTG | GAT | CCC | AAG | AAT | AAT | CTG | GCT | ATT | TTT | 1302 |
| Gln | Val | Ser | Gly | Leu | Ala | Leu | Asp | Pro | Lys | Asn | Asn | Leu | Ala | Ile | Phe | |
| | | | 30 | | | | | 35 | | | | | 40 | | | |
| CAC | AGG | GGG | GAT | CAT | GTC | TGG | GAT | GAA | AAT | TCA | TTT | GAC | AGG | AAC | TTT | 1350 |
| His | Arg | Gly | Asp | His | Val | Trp | Asp | Glu | Asn | Ser | Phe | Asp | Arg | Asn | Phe | |
| | | 45 | | | | | 50 | | | | | 55 | | | | |
| GTT | TAT | CAA | CAA | AGA | GGA | ATC | GGA | CCA | ATC | CAG | GAG | AGC | ACC | ATC | CTT | 1398 |
| Val | Tyr | Gln | Gln | Arg | Gly | Ile | Gly | Pro | Ile | Gln | Glu | Ser | Thr | Ile | Leu | |
| | | 60 | | | | | 65 | | | | | 70 | | | | |
| GTT | GTT | GAT | CCA | AGC | TCC | TCT | AAA | GTC | CTC | AAG | TCA | ACA | GGG | AAA | AAT | 1446 |
| Val | Val | Asp | Pro | Ser | Ser | Ser | Lys | Val | Leu | Lys | Ser | Thr | Gly | Lys | Asn | |
| 75 | | | | | 80 | | | | | 85 | | | | | 90 | |
| TTG | TTT | TTT | TTG | CCC | CAC | GGC | CTG | ACT | ATC | GAC | AGA | GAT | GGG | AAT | TAC | 1494 |
| Leu | Phe | Phe | Leu | Pro | His | Gly | Leu | Thr | Ile | Asp | Arg | Asp | Gly | Asn | Tyr | |
| | | | | 95 | | | | | 100 | | | | | 105 | | |
| TGG | GTC | ACA | GAT | GTA | GCC | CTT | CAT | CAG | GTT | TTC | AAA | TTG | GGA | GCT | GGA | 1542 |
| Trp | Val | Thr | Asp | Val | Ala | Leu | His | Gln | Val | Phe | Lys | Leu | Gly | Ala | Gly | |
| | | | 110 | | | | | 115 | | | | | 120 | | | |
| AAA | GAA | ACA | CCA | CTC | CTT | GTA | TTA | GGG | AGG | GCA | TTT | CAG | CCG | GGG | AGT | 1590 |
| Lys | Glu | Thr | Pro | Leu | Leu | Val | Leu | Gly | Arg | Ala | Phe | Gln | Pro | Gly | Ser | |
| | | 125 | | | | | 130 | | | | | 135 | | | | |
| GAT | CGA | AAA | CAT | TTC | TGT | CAG | CCT | ACT | GAC | GTT | GCA | GTC | GAC | CCA | ATA | 1638 |
| Asp | Arg | Lys | His | Phe | Cys | Gln | Pro | Thr | Asp | Val | Ala | Val | Asp | Pro | Ile | |
| | 140 | | | | 145 | | | | | 150 | | | | | | |
| ACT | GGC | AAC | TTC | TTT | GTG | GCG | GAT | GGC | TAC | TGT | AAC | AGT | CGC | ATC | ATG | 1686 |
| Thr | Gly | Asn | Phe | Phe | Val | Ala | Asp | Gly | Tyr | Cys | Asn | Ser | Arg | Ile | Met | |
| 155 | | | | | 160 | | | | | 165 | | | | | 170 | |
| CAG | TTC | TCA | CCT | AAT | GGA | ATG | TTC | ATC | ATG | CAG | TGG | GGA | GAA | GAA | ACA | 1734 |
| Gln | Phe | Ser | Pro | Asn | Gly | Met | Phe | Ile | Met | Gln | Trp | Gly | Glu | Glu | Thr | |
| | | | | 175 | | | | | 180 | | | | | 185 | | |
| TCC | TCA | AAC | GTT | CCC | AGA | CCT | GGT | CAG | TTC | CGC | ATC | CCG | CAC | AGT | CTG | 1782 |
| Ser | Ser | Asn | Val | Pro | Arg | Pro | Gly | Gln | Phe | Arg | Ile | Pro | His | Ser | Leu | |
| | | | 190 | | | | 195 | | | | | 200 | | | | |
| ACA | ATG | GTA | CCT | GAC | CAG | GGA | CAA | CTA | TGT | GTA | GCC | GAC | AGA | GAG | AAT | 1830 |
| Thr | Met | Val | Pro | Asp | Gln | Gly | Gln | Leu | Cys | Val | Ala | Asp | Arg | Glu | Asn | |

```
                205                         210                          215
GGC  CGG  ATC  CAG  TGC  TTC  CAT  GCT  GAA  ACG  GGC  AAC  TTT  GTC  AAG  CAA       1878
Gly  Arg  Ile  Gln  Cys  Phe  His  Ala  Glu  Thr  Gly  Asn  Phe  Val  Lys  Gln
     220                      225                      230

ATC  AAG  CAT  CAG  GAA  TTC  GGA  AGA  GAG  GTG  TTT  GCT  GTC  TCG  TAT  GCA       1926
Ile  Lys  His  Gln  Glu  Phe  Gly  Arg  Glu  Val  Phe  Ala  Val  Ser  Tyr  Ala
235                      240                      245                      250

CCA  GGT  GGA  GTG  CTG  TAC  GCT  GTT  AAT  GGA  AAG  CCG  TAC  TAT  GGA  TAT       1974
Pro  Gly  Gly  Val  Leu  Tyr  Ala  Val  Asn  Gly  Lys  Pro  Tyr  Tyr  Gly  Tyr
                    255                      260                      265

TCC  GCC  CCT  GTA  CAA  GGC  TTT  ATG  CTG  AAT  TTC  TCC  AAT  GGG  GAT  ATT       2022
Ser  Ala  Pro  Val  Gln  Gly  Phe  Met  Leu  Asn  Phe  Ser  Asn  Gly  Asp  Ile
               270                      275                      280

CTA  GAT  ACC  TTC  ATT  CCT  GCT  AGA  AAG  AAT  TTT  GAC  ATG  CCC  CAT  GAT       2070
Leu  Asp  Thr  Phe  Ile  Pro  Ala  Arg  Lys  Asn  Phe  Asp  Met  Pro  His  Asp
          285                      290                      295

ATT  GCT  GCG  GCA  GAT  GAT  GGA  ACA  GTG  TAT  GTT  GGG  GAT  GCA  CAT  GCC       2118
Ile  Ala  Ala  Ala  Asp  Asp  Gly  Thr  Val  Tyr  Val  Gly  Asp  Ala  His  Ala
     300                      305                      310

AAC  GCA  GTG  TGG  AAG  TTC  TCC  CCT  TCA  AAG  GCC  GAA  CAT  CGA  TCT  GTG       2166
Asn  Ala  Val  Trp  Lys  Phe  Ser  Pro  Ser  Lys  Ala  Glu  His  Arg  Ser  Val
315                      320                      325                      330

AAA  AAA  GCT  GGA  ATA  GAG  GTT  GAA  GAA  ATA  ACA  GAA  ACA  GAG  ATT  TTC       2214
Lys  Lys  Ala  Gly  Ile  Glu  Val  Glu  Glu  Ile  Thr  Glu  Thr  Glu  Ile  Phe
                    335                      340                      345

GAG  ACC  CAT  ATA  AGA  AGC  AGA  CCG  AAG  ACA  AAT  GAG  TCT  GTT  GAG  AAA       2262
Glu  Thr  His  Ile  Arg  Ser  Arg  Pro  Lys  Thr  Asn  Glu  Ser  Val  Glu  Lys
               350                      355                      360

CAA  ACA  CAG  GAG  AAG  CAG  CAG  AAG  CAA  AAG  AAC  AGT  GCT  GGG  GTG  TCT       2310
Gln  Thr  Gln  Glu  Lys  Gln  Gln  Lys  Gln  Lys  Asn  Ser  Ala  Gly  Val  Ser
          365                      370                      375

ACA  CAA  GAG  AAG  CAA  AAT  GTT  GTG  CAA  GAG  ATC  AAT  GCT  GGG  GTG  CCT       2358
Thr  Gln  Glu  Lys  Gln  Asn  Val  Val  Gln  Glu  Ile  Asn  Ala  Gly  Val  Pro
     380                      385                      390

ACA  CAA  GAG  AAG  CAG  AAT  GTT  GTG  CAA  GAG  AGT  AGT  GCT  GGG  GTG  TCT       2406
Thr  Gln  Glu  Lys  Gln  Asn  Val  Val  Gln  Glu  Ser  Ser  Ala  Gly  Val  Ser
395                      400                      405                      410

ACA  CAG  GAG  AAG  CAG  AGT  GTT  GTG  CAA  GAG  AGT  AGT  GCT  GGG  GTG  TCT       2454
Thr  Gln  Glu  Lys  Gln  Ser  Val  Val  Gln  Glu  Ser  Ser  Ala  Gly  Val  Ser
                    415                      420                      425

ACA  CAG  GAG  AAG  CAG  AGT  GTT  GTA  CAA  GAG  AGC  AGC  GCT  GGG  GTG  TCC       2502
Thr  Gln  Glu  Lys  Gln  Ser  Val  Val  Gln  Glu  Ser  Ser  Ala  Gly  Val  Ser
          430                      435                      440

TTC  GTT  CTT  ATC  ATC  ACT  CTT  CTC  ATC  ATT  CCT  ATC  GCA  GTT  CTC  ATT       2550
Phe  Val  Leu  Ile  Ile  Thr  Leu  Leu  Ile  Ile  Pro  Ile  Ala  Val  Leu  Ile
     445                      450                      455

GCC  ATT  GCA  ATC  TTC  ATT  CGC  TGG  AGG  AAA  GTC  AGA  ATG  TAT  GGA  GGT       2598
Ala  Ile  Ala  Ile  Phe  Ile  Arg  Trp  Arg  Lys  Val  Arg  Met  Tyr  Gly  Gly
460                      465                      470

GAC  ATT  GAC  CAC  AAA  TCA  GAA  TCC  AGT  TCA  GTG  GGC  ATT  TTG  GGA  AAA       2646
Asp  Ile  Asp  His  Lys  Ser  Glu  Ser  Ser  Ser  Val  Gly  Ile  Leu  Gly  Lys
475                      480                      485                      490

CTT  AGA  GGG  AAG  GGC  AGC  GGA  GGC  CTT  AAT  CTG  GGA  ACA  TTC  TTT  GCA       2694
Leu  Arg  Gly  Lys  Gly  Ser  Gly  Gly  Leu  Asn  Leu  Gly  Thr  Phe  Phe  Ala
                    495                      500                      505

ACT  CAC  AAA  GGC  TAC  AGT  AGA  AAA  GGC  TTC  GAC  AGG  CTG  AGT  ACA  GAA       2742
Thr  His  Lys  Gly  Tyr  Ser  Arg  Lys  Gly  Phe  Asp  Arg  Leu  Ser  Thr  Glu
          510                      515                      520

GGA  AGT  GAC  CAA  GAG  AAA  GAC  GAT  GAT  GAT  GGC  TCA  GAC  TCT  GAA  GAA       2790
Gly  Ser  Asp  Gln  Glu  Lys  Asp  Asp  Asp  Asp  Gly  Ser  Asp  Ser  Glu  Glu
     525                      530                      535
```

```
GAG TAT TCT GCC CCT CCT ATT CCA CCA GCT CCT GTA TCT TCC TCC         2835
Glu Tyr Ser Ala Pro Pro Ile Pro Pro Ala Pro Val Ser Ser Ser
    540                 545                 550

TGAAACAGTT GACTTCTTCC ATACAACCTT TTGCCCCATT AGCACGTTTA AGATTGTGTA   2895
TTTAAGTGTT ACTGTACTAG TCTGTGGACT GTACAATTGT CATAGTTTTT CCTTTTATTT   2955
TTATTTGAAG TGCTGTTGTA GTCTTTATAT GAACATTCAA AATAATTCTA TTTGGTAGAA   3015
TGACTTTGGC TTTAGAGAGC GTTTTATCCA GTGTTTGATG GCCTTCCTCT GCTTCACCAA   3075
TAGCACTTTA ACTGCCAATT ATTTTCAAGC CTTTAACTGA AAACGAATCG CATTACAAAG   3135
ATATGTGCCA CATAAATGCA AAGCTGCTAA ATCTCTTCTA TTTTTTTAAA TTAACAACAT   3195
GATATTACGT CCAAGAAAGG AAATGATAGA CAAAATATTT AATGTTTCTT ATTTCTTTCT   3255
ATTTTTTTTC TCTTCGTTTT TGGTGTTTAT TGGGATGTCT TATTTTTAGA TGGTTCCACT   3315
GTTTAGAACA CTATTTTCAG AATTTGAATG TACTTTGTGT AATAAAGTGT TCGCAGAGCA   3375
TTACTCTC                                                            3383
```

( 2 ) INFORMATION FOR SEQ ID NO:2:

( i ) SEQUENCE CHARACTERISTICS:
        ( A ) LENGTH: 935 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ser Leu Ser Ser Ser Phe Leu Val Leu Phe Leu Leu Phe Gln
-382        -380            -375                -370

Asn Ser Cys Tyr Cys Phe Arg Ser Pro Leu Ser Val Phe Lys Arg Tyr
    -365            -360                -355

Glu Glu Ser Thr Arg Ser Leu Ser Asn Asp Cys Leu Gly Thr Thr Arg
-350            -345                -340                    -335

Pro Val Met Ser Pro Gly Ser Ser Asp Tyr Thr Leu Asp Ile Arg Met
                -330                -325                -320

Pro Gly Val Thr Pro Thr Glu Ser Asp Thr Tyr Leu Cys Lys Ser Tyr
            -315                -310                -305

Arg Leu Pro Val Asp Asp Glu Ala Tyr Val Val Asp Phe Arg Pro His
        -300                -295                -290

Ala Asn Met Asp Thr Ala His His Met Leu Leu Phe Gly Cys Asn Ile
    -285                -280                -275

Pro Ser Ser Thr Asp Asp Tyr Trp Asp Cys Ser Ala Gly Thr Cys Met
-270                -265                -260                -255

Asp Lys Ser Ser Ile Met Tyr Ala Trp Ala Lys Asn Ala Pro Pro Thr
            -250                -245                -240

Lys Leu Pro Glu Gly Val Gly Phe Arg Val Gly Gly Lys Ser Gly Ser
        -235                -230                -225

Arg Tyr Phe Val Leu Gln Val His Tyr Gly Asn Val Lys Ala Phe Gln
    -220                -215                -210

Asp Lys His Lys Asp Cys Thr Gly Val Thr Val Arg Val Thr Pro Glu
    -205                -200                -195

Lys Gln Pro Gln Ile Ala Gly Ile Tyr Leu Ser Met Ser Val Asp Thr
-190                -185                -180                -175

Val Ile Pro Pro Gly Glu Glu Ala Val Asn Ser Asp Ile Ala Cys Leu
                -170                -165                -160

Tyr Asn Arg Pro Thr Ile His Pro Phe Ala Tyr Arg Val His Thr His
        -155                -150                -145

Gln Leu Gly Gln Val Val Ser Gly Phe Arg Val Arg His Gly Lys Trp
```

-continued

|-140|-135|-130|
|---|---|---|

Ser Leu Ile Gly Arg Gln Ser Pro Gln Leu Pro Gln Ala Phe Tyr Pro
       -125              -120                -115

Val Glu His Pro Val Glu Ile Ser Pro Gly Asp Ile Ile Ala Thr Arg
-110              -105               -100                         -95

Cys Leu Phe Thr Gly Lys Gly Arg Thr Ser Ala Thr Tyr Ile Gly Gly
            -90                   -85                   -80

Thr Ser Asn Asp Glu Met Cys Asn Leu Tyr Ile Met Tyr Tyr Met Asp
        -75                   -70                   -65

Ala Ala His Ala Thr Ser Tyr Met Thr Cys Val Gln Thr Gly Glu Pro
    -60               -55                   -50

Lys Leu Phe Gln Asn Ile Pro Glu Ile Ala Asn Val Pro Ile Pro Val
    -45               -40               -35

Ser Pro Asp Met Met Met Met Met Gly His Gly His His His Thr Glu
-30             -25                  -20                       -15

Ala Glu Pro Glu Lys Asn Thr Gly Leu Gln Gln Pro Lys Arg Glu Glu
                -10                 -5                        1

Glu Glu Val Leu Asp Gln Asp Val His Leu Glu Glu Asp Thr Asp Trp
        5                 10                  15

Pro Gly Val Asn Leu Lys Val Gly Gln Val Ser Gly Leu Ala Leu Asp
    20              25                  30

Pro Lys Asn Asn Leu Ala Ile Phe His Arg Gly Asp His Val Trp Asp
35                  40                  45                      50

Glu Asn Ser Phe Asp Arg Asn Phe Val Tyr Gln Gln Arg Gly Ile Gly
            55                  60                  65

Pro Ile Gln Glu Ser Thr Ile Leu Val Val Asp Pro Ser Ser Lys
            70                  75                  80

Val Leu Lys Ser Thr Gly Lys Asn Leu Phe Phe Leu Pro His Gly Leu
        85              90                  95

Thr Ile Asp Arg Asp Gly Asn Tyr Trp Val Thr Asp Val Ala Leu His
    100             105                 110

Gln Val Phe Lys Leu Gly Ala Gly Lys Glu Thr Pro Leu Leu Val Leu
115             120             125                         130

Gly Arg Ala Phe Gln Pro Gly Ser Asp Arg Lys His Phe Cys Gln Pro
            135                 140                 145

Thr Asp Val Ala Val Asp Pro Ile Thr Gly Asn Phe Phe Val Ala Asp
            150             155                 160

Gly Tyr Cys Asn Ser Arg Ile Met Gln Phe Ser Pro Asn Gly Met Phe
        165             170                 175

Ile Met Gln Trp Gly Glu Glu Thr Ser Ser Asn Val Pro Arg Pro Gly
    180             185                 190

Gln Phe Arg Ile Pro His Ser Leu Thr Met Val Pro Asp Gln Gly Gln
195             200                 205                     210

Leu Cys Val Ala Asp Arg Glu Asn Gly Arg Ile Gln Cys Phe His Ala
            215                 220                 225

Glu Thr Gly Asn Phe Val Lys Gln Ile Lys His Gln Glu Phe Gly Arg
        230             235                 240

Glu Val Phe Ala Val Ser Tyr Ala Pro Gly Gly Val Leu Tyr Ala Val
        245             250                 255

Asn Gly Lys Pro Tyr Tyr Gly Tyr Ser Ala Pro Val Gln Gly Phe Met
    260             265                 270

Leu Asn Phe Ser Asn Gly Asp Ile Leu Asp Thr Phe Ile Pro Ala Arg
275                 280                 285                     290

Lys Asn Phe Asp Met Pro His Asp Ile Ala Ala Asp Asp Gly Thr
                295                 300                 305

```
Val Tyr Val Gly Asp Ala His Ala Asn Ala Val Trp Lys Phe Ser Pro
            310                 315                 320
Ser Lys Ala Glu His Arg Ser Val Lys Lys Ala Gly Ile Glu Val Glu
        325                 330                 335
Glu Ile Thr Glu Thr Glu Ile Phe Glu Thr His Ile Arg Ser Arg Pro
        340                 345                 350
Lys Thr Asn Glu Ser Val Glu Lys Gln Thr Gln Glu Lys Gln Gln Lys
355                 360                 365                 370
Gln Lys Asn Ser Ala Gly Val Ser Thr Gln Glu Lys Gln Asn Val Val
                375                 380                 385
Gln Glu Ile Asn Ala Gly Val Pro Thr Gln Glu Lys Gln Asn Val Val
            390                 395                 400
Gln Glu Ser Ser Ala Gly Val Ser Thr Gln Glu Lys Gln Ser Val Val
        405                 410                 415
Gln Glu Ser Ser Ala Gly Val Ser Thr Gln Glu Lys Gln Ser Val Val
        420                 425                 430
Gln Glu Ser Ser Ala Gly Val Ser Phe Val Leu Ile Ile Thr Leu Leu
435                 440                 445                 450
Ile Ile Pro Ile Ala Val Leu Ile Ala Ile Ala Ile Phe Ile Arg Trp
            455                 460                 465
Arg Lys Val Arg Met Tyr Gly Gly Asp Ile Asp His Lys Ser Glu Ser
            470                 475                 480
Ser Ser Val Gly Ile Leu Gly Lys Leu Arg Gly Lys Gly Ser Gly Gly
        485                 490                 495
Leu Asn Leu Gly Thr Phe Phe Ala Thr His Lys Gly Tyr Ser Arg Lys
    500                 505                 510
Gly Phe Asp Arg Leu Ser Thr Glu Gly Ser Asp Gln Glu Lys Asp Asp
515                 520                 525                 530
Asp Asp Gly Ser Asp Ser Glu Glu Glu Tyr Ser Ala Pro Pro Ile Pro
                535                 540                 545
Pro Ala Pro Val Ser Ser Ser
            550
```

ENZYME AND DNA CODING THEREFOR

FIELD OF THE INVENTION

The present invention relates to a peptidylhydroxyglycine N-C lyase enzyme (PHL), to a DNA molecule encoding PHL, and to the preparation and the use of PHL.

BACKGROUND OF THE INVENTION

Many physiologically active peptides, such as calcitonin, growth hormone releasing factor, LH-RH (luteinizing hormone releasing hormone), vasopressin, gastrin, α-MSH (α-melanotropin) and the like, are active only if their C-terminus is amidated. However, it is difficult to industrially produce the C-terminally amidated peptides directly by a chemical synthesis or a direct genetic engineering process. Their production can be better achieved by a two-step process in which in the first step a non-amidated peptide is produced which is in the second step amidated at its C-terminus. An example of such a process comprises synthesizing a peptide having an additional glycine unit on its C-terminus and converting it in the second step to a C-terminally amidated peptide using a C-terminally amidating enzyme, i.e. a peptidylglycine α-amidating monooxygenase (PAM).

C-terminally amidating enzymes (PAMs) of various origins were purified and corresponding cDNAs were prepared, such as of *Xenopus laevis* skin (Mizuno, K. et al., Biochem. Biophys. Res. Commun. 137, 984–991, 1986; Mizuno, K. et al., Biochem. Biophys. Res. Commun. 148, 546–553, 1987; Ohsuye, K. et al., Biochem. Biophys. Res. Commun. 150, 1275–1281, 1988), porcine pituitary gland (Kizer, J. S. et al., Endocrinology, 118, 2262–2267, 1986), bovine pituitary gland (Murthy, A. S. N. et al., J. Biol. Chem., 261, 1815–1822, 1986; Eipper, B. A. et al., Mol. Endocrinol 1, 777–790, 1987), rat pituitary gland (Mehta, N. M. et al., Arch. Biochem. Biophys., 261, 44–54, 1988; Birtelsen, A. H. et al., Arch. Biochem. Biophys. 279, 87–96, 1990; Stoffers, D. A. et al., Proc. Natl. Acad. Sci. USA 86, 735–739, 1989), and human origin (Glauder, J. et al., Biochem. Biophys. Res. Commun., 169, 551–558, 1990).

The cDNA coding for the C-terminally amidating enzyme PAM originating from the skin of *Xenopus laevis* was inserted into a Baculovirus expression vector system and expressed in insect cells. When the purified enzyme thus prepared acted upon the model peptide Ala-Ile-Gly-Val-Gly-Ala-Pro-Gly prepared by adding a glycine amino acid residue to the C-terminus of a peptide corresponding to the seven amino acid residues of the C-terminus of human calcitonin (hCT), the product formed was not the initially expected amidated peptide (Ala-Ile-Gly-Val-Gly-Ala-Pro-NH$_2$) but a peptide with a C-terminal α-hydroxyglycine residue (Ala-Ile-Gly-Val-Gly-Ala-Pro-Gly-OH) (European Patent Application No. 91810163.5).

Based on this finding, it may be presumed that the physiological C-terminal amidating reaction involves two enzymatic steps, namely the first step which is the α-hydroxylation of the C-terminal glycine of the substrate peptide catalyzed by the hitherto known C-terminally amidating enzyme (PAM) and the second step which is the amidation by cleavage of the N-C bond in the α-hydroxyglycine moiety catalyzed by a another, novel enzyme.

OBJECT OF THE INVENTION

It is the object of the present invention to identify and provide an enzyme catalyzing the cleavage of the N-C bond in the α-hydroxyglycine moiety of a C-terminally α-hydroxyglycylated peptide. Such an enzyme is herein named peptidylhydroxyglycine N-C lyase (PHL).

It is another object of the invention to provide a DNA molecule encoding a PHL and to provide a method for the preparation of a PHL by recombinant DNA technology.

A further object of the invention is to provide a method for the preparation of C-terminally amidated peptides by means of a PHL.

DESCRIPTION OF THE INVENTION

PHL Enzyme and Preparation Thereof From Natural Sources

The invention concerns a peptidylhydroxyglycine N-C lyase (PHL) catalyzing the reaction

wherein R represents a peptide residue, and GlyOH represents an α-hydroxyglycine residue linked to the C-terminus of said peptide R by an amide bond.

In searching for a PHL, a method for activity determination of such an enzyme first had to be established. This method, which is also subject matter of the present invention, comprises (a) adding 2 mM of benzoylhydroxyglycine and a solution containing PHL to MES (2-(N-morpholino)-ethanesulfonic acid) in a final concentration of 100 mM (pH 5.2), (b) carrying out the reaction at 37° C. for 30 minutes, (c) adding perchloric acid to the reaction mixture to stop the reaction, (d) centrifugating of the mixture and (e) determining the product in the supernatant with conventional methods, e.g. by HPLC.

A quantity of PHL enzyme forming 1 pico mole of amidated product per one minute under the above-mentioned conditions is herein defined as "one unit".

With the described method, PHL activities can be measured in various animal tissues. PHL can be shown in animal tissues which are known to contain a PAM enzyme, for example, in *Xenopus laevis* skin or in porcine, bovine, rat or human pituitary glands.

A PHL can be purified from such tissue by conventional methods, e.g. comprising homogenization of the tissue, chromatography such as ion-exchange, hydrophobic or size-exclusion chromatography, precipitation, e.g. with ammonium sulfate or acid, preparative electrophoresis such as SDS-gel electrophoresis or isoelectric focussing, and the like. A preferred process for the purification of PHL from *X. laevis* skin is described in Example 1. It comprises an ammonium sulfate precipitation and the use of a DEAE-Sepharose CL-6B column, of a Superose 12 molecular sieve column and of a MonoQ column.

The amino acid sequence of a PHL isolated from a natural source can be determined according to conventional methods, for example with an automatic gas phase amino acid sequencer.

The sequence of the N-terminus of the PHL from *X. laevis* and of tryptic fragments thereof was determined. The sequences correspond to amino acid sequences downstream of position 383 (Glu, N-terminus of PHL)

in the sequence given in the sequence listing under Sequence Identification Number (SEQ ID No.) 1.

A polypeptide having the amino acid sequence of the PHL obtainable from *X. laevis* skin, hereinafter also simply referred to as the PHL from *X. laevis*, is the most preferred embodiment of the present invention. The whole amino acid sequence of the natural PHL from *X. laevis* extends from position 383 up to an amino acid in about position 706 or 713. However, a PHL within the meaning of the invention is not only a naturally occurring PHL but also any polypeptide with PHL activity. Such a polypeptide can be derived from a DNA sequence encoding a naturally occurring PHL or from a fragment or mutant thereof.

Therefore, the invention concerns also longer polypeptides with PHL activity, e.g. such starting at an amino acid from about position 363 to about 383 and extending up to any amino acid in about position 706 up to about position 935 of the sequence encoded by the DNA with SEQ ID No. 1. Longer polypeptides with PHL activity also may be prolonged with amino acid sequences not directly attached thereto in nature, e.g. derived from *E. coli* proteins such as TrpE or β-galactosidase or also amino acids encoded by DNA regions located in the neighbourhood of the PHL coding region. A polypeptide of the latter type is, for example, encoded by the coding region inserted in the vector pVL-PHL prepared according to example 3. This polypeptide is composed of the amino acids 1 to 60 and 363 to 760 of the amino acid sequence encoded by the DNA with the SEQ ID No. 1. The invention preferentially concerns the polypeptides with PHL activity which start at about position 363 or 383 and extend up to about position 706, 713, 760or 935. Most preferred are the proteins which correspond to the naturally occurring form, i.e. starting in position 383 and ending in position 706 or 713, and those which are encoded by the insert of vector pVL-PHL.

The naturally occuring PHL from *X. laevis* is further characterized in that (1) it catalyzes the reaction

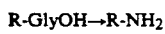

wherein R represents a peptide residue, and GlyOH represents an α-hydroxyglycine residue linked to the C-terminus of said peptide R by an amide bond;

(2) its molecular weight is about 37 KDa as measured by SDS-polyacrylamide gel electrophoresis;

(3) its optimum working pH is about 5.4;

(4) as for its stability to pH, it is most stable at a pH value of about 8.5, when allowed to stand at 4° C. for 24 hours;

(5) as for the influence of temperature on its activity, it exhibits the highest activity at 37° C., even though it exhibits a substantial activity also at 30° C. and 42° C.; and (6) it is stabilized by glycerol and ethylene glycol.

DNA Encoding PHL and Production Thereof by Recombinant DNA Technology

PHL is useful for the production of physiologically active peptides having an amide structure on its C-terminus, and therefore large amounts of PHL must be acquired for industrial use. However, it is difficult to acquire large amounts from natural sources such as from the skin of *Xenopus laevis*, and therefore the production of PHL by a genetic engineering method is desirable. A prerequisite for the production of a PHL by genetic engineering is the availability of a DNA molecule encoding the PHL.

For the purpose of producing a PHL by genetic engineering, the present invention also concerns a recombinant DNA molecule coding for a PHL and a method for the preparation of such a recombinant DNA molecule. Such a recombinant DNA molecule is preferentially a hybrid vector comprising a DNA sequence encoding a PHL, preferably the PHL from *X. laevis*. However, the invention relates also to manufactured DNA molecules encoding PHL which are not hybrid vectors but which can be used for the preparation thereof, for example DNA fragments excised from hybrid vectors, optionally together with flanking sequences such as linkers or vector sequences, or also synthetic DNA molecules.

The hybrid vectors of the invention are useful for cloning and/or expressing a PHL gene in hosts, such as bacteria, fungi or higher eucaryotic cells. They may be derived from any vector useful in the art of genetic engineering, such as from viruses, phages, cosmids, plasmids or chromosomal DNA, for example derivatives of SV40, Herpes-viruses, Papiloma viruses, Retroviruses, Baculovirus, phage λ, e.g. NM 989 or EMBL4, or phage M13, bacterial plasmids, e.g. pBR322, pUC18, pSF2124, pBR317 or pPLMu., or yeast plasmids, e.g. yeast 2μ plasmid, or also chromosomal DNA comprising an origin of replication or an autonomously replicating sequence (ARS), or a defective virus, phage or plasmid in the presence of a helper virus, phage or plasmid allowing replication of said defective virus, phage or plasmid, e.g. M13(+)KS vector in presence of e.g. M14K07 helper phage. The Baculoviruses which can be used in the present invention are, for example, *Autographa californica* nuclear polyhedrosis virus (AcMNPV), *Trichoplusia ni* MNPV, *Rachiplusia ou* MNPV, *Galleria mellonella* MNPV, *Bombyx mori* nuclear polyhedrosis virus (BmNPV), and the like. A kit comprising a combination of an *Autographa californica* nuclear polyhedrosis virus and baculovirus transfer vectors pAc700, pAc701, pAc702, pVL1392 and pVL1393 is commercially available from Invitrogen.

A suitable vector for the production of a hybrid vector of the invention is a vector which is operable in the microbial host cell chosen for multiplying the hybrid vector or for the expression of PHL. Suitable vectors contain a complete replicon and a marker gene, which renders possible the selection and identification of the microorganisms transformed by the expression plasmids by means of a phenotype feature.

Thus, the hybrid vectors of the invention provide for replication of a desired DNA in a suitable host, either as an extrachromosomal element or by integration in the host chromosome. Several possible vector systems are available for integration and expression of the cloned DNA of the invention. In principle, all vectors which replicate and/or comprise a recombinant PHL gene from which PHL can be expressed in the chosen host are suitable. The vector is selected depending on the host cells envisaged for transformation. In general, such host cells may be prokaryotic or eukaryotic microorganisms such as bacteria, fungi such as yeasts or filamentous fungi, or cells of higher eukaryotic origin such as animal, for example mammalian or insect, cells. Suitable host cells will be discussed in detail hereinbelow. In principle, the hybrid vectors of the invention comprise a DNA encoding PHL, an origin of replication or an autonomously replicating sequence, optionally dominant marker sequences, and, optionally, additional restriction sites.

An origin of replication or an autonomously replicating sequence (a DNA element which confers autonomoulsy replicating capabilities to extrachromosomal elements) is provided either by construction of the vector to include an exogeneous origin such as derived from Simian virus (SV 40) or another viral source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers are particularly genes from which a polypeptide can be expressed which provides resistance against compounds toxic to the receipt organism or which completes the enzyme system of a mutant lacking such an essential polypeptide, e.g. of an auxotrophic mutant. Suitable marker genes express, for example, antibiotic resistance, e.g. against tetracycline, ampicillin, or cycloheximide, or provide for prototrophy in an auxotrophic mutant, for example in a yeast deficient in the ura3, leu2, his3 or trp1 gene. It is also possible to employ as markers structural genes which are associated with an autonomously replicating segment providing that the host to be transformed is auxotrophic for the product expressed by the marker.

The DNA encoding a PHL inserted in a hybrid vector of the invention consists of cDNA isolated from a suitable cDNA library, e.g. from human, porcine, rat or bovine, preferably from the pituitary gland thereof, or from frog, preferably from $X$. $laevis$ skin. DNA encoding PHL may, however, also consist of genomic DNA, e.g. isolated from a suitable genomic DNA library, e.g. from human, porcine, rat or bovine cells, or preferably from $X$. $laevis$ cells. DNA encoding PHL may further consist of chemically synthesized DNA having the DNA sequence either of a naturally occurring PHL encoding DNA or of a mutant thereof.

A preferred recombinant DNA molecule of the invention comprises a DNA of the sequence with the SEQ ID No. 1 or a fragment or mutant thereof encoding a polypeptide of the invention with PHL activity, preferentially a preferred polypeptide of the invention.

Such a fragment is e.g. the DNA molecule encoding the whole PHL moiety of the AE-III protein encoded by the DNA sequence with SEQ ID No. 1. Said fragment extends from nucleotide position 1177 up to 2148 or 2169. However, also shorter or longer DNA fragments may encode polypeptides with PHL activity, e.g. those starting at any nucleotide from position 31 to 1117 and ending at any nucleotide in position 2148 to 2835.

A mutant of the naturally occurring DNA is encoding a naturally occurring PHL or a variant form thereof having PHL activity. A mutant according to the present invention may also be a deletion mutant of the DNA with the SEQ ID No. 1. A preferred example of such a deletion mutant is the insert of the vector pVL-PHL or the recombinant Baculovirus expression vector AcPHL consisting of the sequences extending from 1 to 210 and 1117 to 2310 of the sequence with SEQ ID No. 1. However, a mutant DNA encoding a naturally occurring PHL is also intended to be a silent mutant wherein one or more nucleotides are replaced by other nucleotides, whereby the new codons code for the same amino acid(s). Such a mutant DNA sequence is also a degenerated DNA sequence. Degenerated DNA sequences are degenerated within the meaning of the genetic code in that an unlimited number of nucleotides are replaced by other nucleotides without changing the amino acid sequence for which they code. Such degenerated DNA sequences may be useful because of their different restriction sites and/or of their frequency of particular codons which are preferred by a particular host to obtain optimal expression of PHL.

Host strains for the multiplication of the hybrid vectors of the invention are, for example, strains of yeast or preferentially of $E.$ $coli.$ Within the meaning of hybrid vectors of the invention are also hybrid expression vectors for the expression of PHL, herein also named hybrid expression vectors. They have in general the same features as the hybrid vectors described hereinbefore, and additionally comprise the PHL gene operably linked with expression control sequences allowing the production and, optionally, the secretion of PHL. Thus, hybrid expression vectors of the invention comprise a promoter region operably linked with a structural gene encoding a PHL, preferentially the PHL from $X.$ $laevis$, and optionally a DNA fragment encoding a leader or signal peptide, a transcriptional enhancer, a ribosomal binding site, a transcriptional terminator region and/or further regulatory sequences.

A wide variety of promoter sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host.

Examples for suitable promoters are $\lambda P_L$, $\lambda P_R$, or $\lambda N$, $E.$ $coli$ lac, trp, tac, or lpp, yeast TRIP1-, ADHI-, ADHII-, PHO3-, PHO5-, or glycolytic promoters such as the promoter of the enolase, glyceraldehyde-3-phosphate dehydrogenase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or promoters derived from eukaryotic viruses, e.g. SV40, Rous sarcoma virus, adenovirus 2, bovine papilloma virus, papovavirus, cytomegalovirus or Baculovirus, e.g. $Autographa$ $californica$ nuclear polyhedrosis virus (AcMNPV), $Trichoplusia$ $ni$ MNPV, $Rachiplusia$ $ou$ MNPV, $Galleria$ $mellonella$ MNPV, derived promoters or mammalian cell derived promoters, e.g. of the actin, collagen, myosin, or $\beta$-globin gene. A preferred eukaryotic promoter is a polyhedrin gene promoter of a Baculovirus, preferentially of the $Autographa$ $californica$ nuclear polyhedrosis virus (AcMNPV). The eukaryotic promoters may be combined with enhancing sequences such as the yeast upstream activating sequences (UAS) or viral or cellular enhancers such as the cytomegalovirus IE enhancers, SV40 enhancer, immunoglobulin gene enhancer or others.

Enhancers useful for the expression of PHL are transcription-stimulating DNA sequences, e.g. derived from viruses such as Simian virus, Cytomegalovirus, polyoma virus, bovine papilloma virus or Moloney sarcoma virus, or of genomic origin. An enhancer sequence may also be derived from the extrachromosomal ribosomal DNA of *Physarum polycephalum* (PCT/EP 8500278), or it may be the upstream activation site from the acid phosphatase PHO5 gene (EP Appl. No. 86 111 820.6), or the PHO5, trp, PHO5-GAPDH hybrid (EP Appl. No. 86 111 820.6), or the like promoter.

Signal sequences which can be used for the present invention may be, for example, a presequence or secretory leader directing the secretion of the polypeptide, or the like. Signal sequences are known from literature, e.g. those compiled in von Heijne, G., Nucleic Acids Res. 14, 4683 (1986). Another signal sequence extends from amino acid 1 to 21 of the amino acid sequence depicted in the sequence listing under SEQ ID No. 1.

A ribosomal binding site (Shine-Dalgarno Sequence) is either naturally linked to the promoter used or may be located on a short nucleotide sequence which may be covalently linked 5' to the region coding for PHL. Ribosomal binding sites are known in the art.

A promoter chosen for the construction of hybrid expression vector of the invention may be regulated by a regulatory protein and the production of PHL in the transformed host cell then may be inducible or derepressible. The gene for the regulatory protein may be located either in the genome of the host strain, on an additional plasmid vector the host strain may be co-transformed with, or on the hybrid vector of the invention. The selection of a suitable gene for a regulatory protein depends on the promoter used. The conditions for the induction or derepression of the production of PHL also depend on the promoter and on the regulatory protein. A regulatory protein which can be used in the present invention is, for example, a repressor protein, e.g. a product of the trpR, lacI, λcro, or λcI gene, or a temperature sensitive mutant thereof.

Preferred hybrid vectors of the invention are pAE-III-202-4, pVL-PHL and baculovirus AcPHL described hereinafter in the examples.

The invention also concerns a process for the preparation of a recombinant DNA molecule defined hereinbefore. Such a process comprises a) isolating genomic DNA from suitable cells, and selecting the desired DNA, e.g. using a DNA probe or using a suitable expression system and screening for expression of PHL; or b) isolating mRNA from suitable cells, selecting the desired mRNA, e.g. by hybridization with a DNA probe or by expression in a suitable expression system and screening for expression of PHL, preparing single-stranded cDNA complementary to that mRNA, then double-stranded cDNA therefrom; or c) isolating cDNA from a cDNA library and selecting a cDNA fragment encoding PHL, e.g. using a DNA probe or using a suitable expression system and screening for expression of the desired polypeptide; or d) incorporating the DNA of step a), b) or c) into an appropriate vector, transforming appropriate host cells with the obtained hybrid vector, selecting transformed host cells which contain the desired DNA from untransformed host cells and multiplicating the transformed host cells, and isolating the desired DNA.

The invention also concerns a process for the preparation of a recombinant DNA molecule defined hereinbefore comprising excising a DNA fragment encoding PHL from a hybrid vector of the invention, optionally together with flanking sequences derived from the vector or linker sequences.

The invention also concerns a process for the preparation of a recombinant DNA molecule defined hereinbefore comprising synthesizing a DNA molecule encoding a PHL in vitro by chemical synthesis.

Genomic DNA may be isolated and screened for the desired DNA (step a). Genomic DNA is isolated from a cell containing a PHL gene. A genomic DNA library is prepared therefrom by digestion with suitable restriction endonucleases and incorporation into suitable vectors following established procedures. The genomic DNA library is screened with a DNA probe, or expressed in a suitable expression system and the obtained polypeptides screened in the manner described hereinbefore.

Polyadenylated messenger RNA (step b) is isolated from the suitable cells by known methods. Isolation methods involve, for example, homogenizing in the presence of a detergent and a ribonuclease inhibitor, e.g. heparin, guanidinium isothiocyanate or mercaptoethanol, extracting the mRNA with suitable chloroform-phenol mixtures, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo(U) sepharose. Preferably, such purified total mRNA is fractionated according to size by gradient centrifugation, e.g. in a linear sucrose gradient, or chromatography on suitable size fractionation columns, e.g. on agarose gels. The desired mRNA is selected by screening the mRNA directly with a DNA probe, or by translation in suitable cells or cell-free systems and screening for the production of PHL.

Fractionated mRNA may be translated in cells, e.g. frog oocytes, or in cell-free systems, e.g. in reticulocyte lysates or wheat germ extracts. The obtained polypeptides are screened for enzymatic activity or for reaction with antibodies raised against the native polypeptide, e.g. in an immunoassay, for example radioimmunoassay, enzyme immnoassay or immunoassay with fluorescent markers. Such immunoassays and the preparation of polyclonal and monoclonal antibodies are well known in the art and are applied accordingly.

The preparation of a single-stranded complementary DNA (cDNA) from the selected mRNA template is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridizing with the poly(A) tail of the mRNA and a suitable enzyme such as a reverse transcriptase e.g. from avian myeloblastosis virus (AMV). After degradation of the template mRNA e.g. by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of *E. coli* DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a randomly cloned cDNA library and screened for the desired cDNA (step c). The cDNA library is constructed by isolating mRNA from suitable cells, and preparing single-stranded and double-stranded cDNA therefrom as described above. This cDNA is digested with suitable resctriction endonucleases and incorporated into λ phage, e.g. λ charon 4A or λ gt11 following established procedures. The cDNA library replicated on nitrocellulose membranes is screened by using a DNA probe, or expressed in a suitable expression system and the obtained polypeptides screened for reaction with an antibody with PHL specificity or for PHL enzymatic activity.

The selection of the desired DNA or mRNA is preferably achieved using a DNA hybridization probe, thereby avoiding the additional step of translation. Suitable DNA probes are DNAs of known nucleotide sequence consisting of at least 17 nucleotides, for example synthetic DNAs, cDNAs derived from mRNA coding for PHL, or genomic DNA fragments comprising e.g. adjacent DNA sequences which are isolated from a natural source or from a genetically engineered microorganism.

Synthetic DNA probes are synthesized according to known methods, preferably by stepwise condensation using the solid phase phosphotriester, phosphite triester or phosphoramidite method, e.g. the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridization, the DNA probes are labelled, e.g. radioactively labelled by the well known kinase reaction. The hybridization is performed according to known procedures, i.e. in buffer and salt solutions containing adjuncts, e.g. calcium chelators, viscosity regulating compounds, proteins, non-homologous DNA and the like, at temperatures favoring selective hybridization, e.g. between 0° C. and 80° C., for example between 25° C. and 50° C. or around 65° C.

A variety of methods are known in the art for the incorporation of double-stranded cDNA or genomic DNA into an appropriate vector (step d). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possibilities are the addition of synthetic linkers to the termini of the double-stranded DNA, or the incorporation of the double-stranded DNA into the vector by blunt- or staggered-end ligation. Appropriate vectors will be discussed in detail hereinbelow.

The transformation of appropriate host cells with the obtained hybrid vector (step e) and the selection and multiplication of transformed host cells (step f) are well known in the art. Examples for such methods are given further below. Hybrid vectors and host cells may be particularly suitable for the production of DNA, or else for the production of the desired polypeptides.

The preparation of the desired DNA is achieved by methods known in the art, e.g. extraction with phenol and/or chloroform. Optionally, the DNA can be further manipulated e.g. by treatment with mutagenic agents to obtain mutants, or by digestion with restriction enzymes to obtain fragments, modify one or both termini to facilitate incorporation into the vector, and the like.

The nucleotide sequence of a DNA according to the invention can be determined by methods known per se, for example by the Maxam-Gilbert method using end-labelled DNA or by the dideoxy chain termination method of Sanger.

PHL gene sequences of the present invention can also be prepared by an in vitro synthesis according to conventional methods. Suitable methods for the synthesis of DNA have been presented in summary form by S. A. Narang (Tetrahedron 39, 3, 1983). The known synthesis techniques allow the preparation of polynucleotides up to 120 bases in length, in good yield, high purity and in a relatively short time. Suitably protected nucleotides are linked with one another by the phosphodiester method (K. L. Agarwal et al., Angew. Chemie 84, 489, 1972), the more efficient phosphotriester method (C. B. Reese, Tetrahedron 34, 3143, 1972), the phosphite triester method (R. L. Letsinger et al., J. Am. Chem. Soc. 98, 3655, 1976) or phosphoramidite method (S. L. Beaucage and M. H. Carruthers, Tetrahedron 22, 1859, 1981). Simplification of the synthesis of the oligonucleotides and polynucleotides is made possible by the solid phase method, in which the nucleotide chains are bound to a suitable polymer. H. Rink et al. (Nucl. Acids Research 12, 6369, 1984) use trinucleotides instead of individual nucleotides and link them by the phosphotriester method in the solid phase synthesis. A polynucleotide can thus be prepared in a short time and with good yields. The actual double-stranded DNA is built up enzymatically from chemically prepared overlapping oligonucleotides from both DNA strands, which are held together in the correct arrangement by base-pairing and are then chemically linked by the enzyme DNA ligase. Another possibility comprises incubating overlapping single oligonucleotides from the two DNA strands in the presence of the four required deoxynucleoside triphosphates with a DNA polymerase, for example DNA polymerase I, the Klenow fragment of polymerase I or T4 DNA polymerase, or with AMV (avian myeloblastosis virus) reverse transcriptase. The two oligonucleotides are thereby held together in the correct arrangement by base-pairing and are supplemented with the required nucleotides by the enzyme to give a complete double-stranded DNA (S. A. Narang et al., Anal. Biochem. 121, 356, 1982).

The process for the preparation of a DNA molecule of the invention is hereinafter exemplified for a hybrid vector comprising a DNA fragment encoding the polypeptide AE-III, a precursor of the *Xenopus laevis* PHL enzyme. The said DNA fragment has the DNA sequence with SEQ ID No. 1.

Total RNA can be prepared from a natural source of a PHL, e.g. the skin of *Xenopus laevis*, by standard methods. Next, poly(A)RNA can be prepared from the total RNA in conventional manner, e.g. by the use of an oligo(dT)-affinity column such as oligo(dT)-latex (Takara Shuzo). cDNA can be prepared according to conventional methods, e.g. to the procedure of Gubler, U. et al.; Gene, 25, 263-269 (1983). After linking a linker. e.g. an EcoRI linker, to the cDNA, the cDNA can be inserted into a cloning vector, e.g. into the EcoRI site of phase λgt 10. If a cosmid or λ-phage is used as cloning vector, and an in vitro packaging reaction is to be carried out in conventional manner. Then a suitable host such as *E. coli* can be transformed according to conventional methods in order to prepare a cDNA library.

Then, a clone expected to include the cDNA coding for the objectiv PHL can be screened out according to conventional screening strategies, for example by searching in the library for enzymatic activity, binding of specific antibodies or hybridization of the DNA with labelled DNA probes which are homologous to DNA sequences of the PHL gene. The sequence of the DNA probe, which can be, for example, a synthetic oligonucleotide, can be predetermined by determining part of the PHL amino acid sequence and deducing the corresponding DNA sequences.

The comparison of the PHL from *X. laevis* skin with the amino acid sequence of the PAM enzyme AE-II from *X. laevis* skin presumed from the nucleotide sequence of cDNA (Ohsuye, K. et al., Biochem. Biophys. Res. Commun. 150, 1275-1281, 1988) shows that both enzymes share sections with homologous sequences.

Thus, in the present case, it is also possible to use a restriction fragment of AE-II cDNA in order to prescreen the library for clones carrying PHL DNA. A 814 bp long Xba I (1191)-Xba I (2004) fragment of AE-II cDNA obtained according to Ohsuye et al. (op. cit.) was labelled with [$\alpha$-$^{32}$P] dCTP by means of Random Primed DNA Labeling Kit (Boehringer Mannheim Co.) and used as probe. In the present specification, this probe is referred to as "AE-II-Xba". In the present case a cDNA library consisting of about $2.5 \times 10^5$ clones was screened to obtain 13 positive clones.

Since the positive clones included of course also AE-II cDNA clones, the objective clone coding for PHL had to be screened in a second step. Due to the differences in the amino acid sequences of AE-II and PHL it was predictable that an EcoR V-cleaved site of AE-II cDNA is not present but a Kpn I-cleaved site may exist in the cDNA coding for PHL. Thus, the inserted DNA fragment of the positive clones were directly amplified from the phage DNA obtained from the plaque on the plate by the PCR method of Saiki, R. K. et al.: Science, 239, 487-491 (1988), and screened by digesting it with the two restriction enzymes EcoR V and Kpn I.

As the result, among the 13 positive clones, 4 clones were found to be of PHL type. A clone conceivably having the longest coding region was screened out and named "AE-III-101/λgt 10".

In order to obtain a further longer cDNA clone, a 0.5 kb fragment of EcoR I-BamH I located in the 5' side of the cDNA insert of clone AE-III-101/λgt 10 was labelled with [$\alpha$-$^{32}$P] dCTP to obtain a second probe AE-III-Bam. Using both probes AE-II-Xba and AE-III-Bam, the cDNA library was screened to obtain clones hybridizing with both probes. In the same manner as in the above-mentioned case, their inserted DNA fragments were directly amplified by PCR method and analyzed with restriction enzymes EcoR V and Kpn I to reveal clones of PHL type. Among them, a clone conceivably having the longest coding region was screened out and named AE-III-202/λgt 10.

Next, DNA sequences of the cDNA insert of clone AE-III-202/λgt 10 was determined in conventional manner. The sequence is shown in the sequence listing under SEQ ID No. 1. The cDNA insert of AE-III-202 is constituted of 3383 bp and comprises the reading frame starting with the ATG codon in base position 31 and ending at the stop codon TGA in base position 2838 which codes for an amino acid sequence of 935 amino acids. The peptide having this amino acid sequence is named AE-III. In the structure of AE-III, a hydrophobic region which presumably is a signal peptide or part thereof extends from amino acid position 1 up to 21 and the amino acid sequence corresponding to a preferred protein with PHL activity of the present invention extends from about position 363 to 383 (Glu) up to any amino acid from position 706 (Lys) up to 935 (Ser), most preferentially from about 383 up to positions 706, 713 or 935. Other preferred proteins with PHL activity are that consisting of amino acids 1 to 760 or 1 to 59 and 363 to 760 and being encoded by the inserts of the vectors pVL-AE-III or pVL-PHL, respectively. The naturally occurring mature *X. laevis* PHL is thus formed by processing of the precursor AE-III.

A DNA molecule comprising the AE-III gene coding for a precursor of PHL can be used for producing said precursor by a recombinant DNA technique. By appropriately shortening it and inserting it into an expressing vector, it can be used for directly producing a preferred protein with PHL activity as defined above, but also other proteins with PHL activity having a shortened C-terminus or N-terminus, and other various modified PHL enzymes.

Transformed Hosts and Preparation Thereof

The invention concerns a transformed host cell for multiplicating a recombinant DNA molecules of the invention or particularly for expressing a PHL structural gene comprised in a recombinant DNA molecule of the invention.

The transformed microbial host strains are cultured in a liquid medium containing sources of carbon and nitrogen which can be assimilated by the microbial cell, and inorganic salts, applying methods known in the art. The culturing of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae*, *Kluyveromyces lactis*, or filamentous fungi, such as *Aspergillus spec.*, e.g. *A. nidulans, A. oryzae, A. carbonarius, A. awamori* or *A. niger*. However, the use of suitable hosts which are devoid of or poor in restriction enzymes or modification enzymes may be advantageous. Examples of such hosts are bacteria, e.g. *Bacillus subtilis, Bacillus stearothermophilus, Pseudomonas, Haemophilus, Streptococcus* and others, and yeasts, for example *Saccharomyces cerevisiae*, and in particular strains of *Escherichia coli*, for example *E. coli* X1776, *E. coli* Y1090, *E. coli* W3110, *E. coli* HB101/LM1035, *E. coli* JA 221, *E. coli* DH5α, or preferentially *E. coli* DH5αF', JM109, MH1 or HB101, or *E. coli* K12 strain. Further suitable hosts are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells. Other suitable host cells are established insect cell lines, for example, *Spodoptera frugiperda*, such as Sf21 or preferentially Sf9 (ATTC CRL1711), *Mamestra brassicae*, *Bombyx mori* cell systems using *Bombyx mori* nuclear polyhedrosis virus (BmNPV) and the like.

A preferred transformed host is *E. coli* HB101 transformed with plasmid pAE-III-202-4, pVL-AE-III or pVL-PHL described hereinafter in the Examples. Another preferred transformed host is *Spodoptera frugiperda* Sf9 (ATTC CRL 1711) transformed with the recombinant baculovirus AcPHL and AcAE-III prepared in Example 3.

The invention concerns also a method for the preparation of such transformed hosts comprising treatment of a suitable host cell under transforming conditions with a recombinant DNA molecule of the present invention, especially a hybrid vector of the invention, optionally together with a selection marker gene and optionally selecting the transformants.

Transformation of microorganisms is carried out according to conventional methods as described in the literature, for example for *S. cerevisiae* (A. Hinnen et al., Proc. Natl. Acad. Sci. USA, 75, 1929, 1978), for *B. subtilis* (Anagnostopoulos et al., J. Bacteriol. 81, 741, 1961), and for *E. coli* (M. Mandel et al., J. Mol. Biol. 53, 159, 1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably so chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of the said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum titer of the polypeptide or derivative of the invention is obtained. Thus, an *E. coli* or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

Production of PHL

The present invention concerns also a method for the production of PHL.

One embodiment is a process for the preparation PHL from natural sources according to conventional methods as described above. A second embodiment is the preparation of PHL by a method comprising expressing a structural gene coding for a polypeptide with PHL activity or, optionally, a precursor thereof which can be processed in vivo or in vitro to liberate such a polypeptide in a suitable transformed host and isolating the produced polypeptide with PHL activity, optionally after processing an expressed precursor.

For the expression of PHL, either procaryotic or eucaryotic host cells may be used, e.g. *E. coli* strains defective in protease genes, e.g. in the lon protease gene, and genes involved in the regulation of heat shock induced protein synthesis, e.g. in the htpR gene (U.S.

Pat. No. 4,758,512; Buell, G. et al., Nucleic Acids Res. 13: 1923-1938, 1985).

According to another embodiment of the present invention, a DNA coding for the present enzyme, such as cDNA, is inserted into a baculovirus transfer vector to construct a recombinant baculovirus transfer vector, and the recombinant baculovirus transfer vector is then co-transfected with a baculovirus DNA to insect cells to carry out a homologous recombination. The baculovirus transfer vector is usually a plasmid containing a segment of baculovirus DNA, which segment comprises a gene not essential for the replication of bacolovirus. The gene not essential for the replication of baculovirus is, for example, a polyhedrin gene comprising a polyhedrin structure gene and a promoter thereof. Such baculovirus transfer vectors are, for example, pAcYM1 (Matsuura, Y., et al., J. Gen. Virol. (1987) 68, 1233-1250), pAc311, pAc360, pAc373, pAc380 (U.S. Pat. No. 4,745,051), pAc700, pAc701, pAc702, pVL1392, pVL1393, and the like. Preferred is the use of pVL1392.

The baculoviruses used in the present invention are, for example, *Trichoplusia ni* MNPV, *Rachiplusia ou* MNPV, *Galleria mellonella* MNPV, and the like. Preferentially used is *Autographa californica* nuclear polyhedrosis virus (AcMNPV). A kit comprising a combination of an *Autographa californica* nuclear polyhedrosis virus and baculovirus transfer vectors pAc700, pAc701, pAc702, pVL1392 and pVL1393 is commercially available from Invitrogen Corp., San Diego, Calif., USA. The insect cells used in the present invention are established insect cell lines, for example, *Spodoptera frugiperda*, such as Sf21 or preferentially Sf9 (ATTC CRL1711), but also *Mamestra brassicae* and the like. A *Bombyx mori* cell system using *Bombyx mori* nuclear polyhedrosis virus (BmNPV) can also be used in the present invention.

The homologous recombination is carried out in accordance with a conventional procedure as described, for example, in "A Manual of Methods for Baculovirus Vectors and Insect Cell Culture Procedures, M. D. Summers, Texas Agricultural Experiment Station Bulletin No. 1555". The transfected insect cells are cultured in accordance with a conventional procedure. Namely, the transfected insect cells may be cultured in any tissue culture medium in which insect cells can grow, such as Grace's or TC100 medium supplemented with mammalian serum, serum-free medium EX-CELL400, or the like, at a temperature of 20° C. to 30° C., preferably 27° C. to 28° C., for example 27° C., for 2 to 10 days, preferably 3 to 5 days.

According to the present invention, expressed PHL enzyme may be secreted into the culture supernatant, and then can be recovered from the culture supernatant according to a conventional procedure, such as centrifugation, a salting out technique, or various chromatographic procedures, or a combination thereof. However, the expressed protein may also stay attached to the producing cell, e.g. intracellularly or in a periplasmatic space, and then can be recovered by conventional method in which the cells are disintegrated.

Preparation of C-terminally Amidated Peptide by Means of PHL

The invention also concerns a method for effectively producing a C-terminally amidated peptide from a peptide having a glycine residue on its C-terminus by a combined use of hitherto known C-terminal amidating enzyme PAM and a polypeptide of the invention with PHL activity, preferentially the PHL of *X. laevis* or a fragment or mutant thereof.

The present invention further relates to a method for producing a peptide having an amidated C-terminus which comprises treating a peptide having an α-hydroxyglycine on the C-terminus with a PHL, preferentially such having an amino acid sequence extending from about position 1 to 383 or more preferentially 363 to about 383 up to any amino acid in about position 706 to about 935, preferentially .706, 713 or 935, of the sequence depicted under SEQ ID No. 1 in the Sequence listing hereinafter.

A PHL enzyme of the invention can be used alone for converting a C-terminal α-hydroxyglycine-containing peptide, e.g. C-terminal α-hydroxyglycine-containing human calcitonin precursor hCT-GlyOH, into the corresponding C-terminal amidated peptide. If a PHL enzyme is used in combination with a hitherto known C-terminal amidating enzyme PAM, the reaction can start also with C-terminally glycine extended peptides, e.g. the corresponding human calcitonin precursor hCT-Gly. In the latte case, PAM transforms the glycine unit of a peptide having glycine on its C-terminus to a α-hydroxyglycine unit and the PHL enzyme converts this intermediate peptide to a C-terminally amidated peptide. Thus, a C-terminally amidated peptide can be produced from a C-terminal glycine-containing peptide with a high efficiency by a combined use of these two enzymes, whereby the enzymes may be used together in one step or sequentially in a two-step process.

If the two enzymes are combined in one reaction mixture, the adopted reaction conditions such as co-operative factors, pH, temperature, etc. must be suitable for both the PAM and PHL enzymes and both enzymes must be relatively close to each other in optimum pH, optimum temperature, etc. If the two enzymes are allowed to react sequentially in two different steps, they may differ in their optimal reaction conditions such as co-operative factors, optimum pH, optimum temperature, etc., because individual reaction conditions can be chosen for each step. In the preferred embodiments of the invention the enzymes used are the PAM and PHL derived from *Xenopus laevis*. When PAM from *Xenopus laevis* is used in a one-step process together with the PHL from *Xenopus laevis*, copper ion, ascorbic acid, KI and catalase must be used as co-operative factors, the preferable pH of the reaction mixture is about 5.5 to about 6.0 and the preferable reaction temperature is about 25° C. to about 35° C. When only the PHL from *Xenopus laevis* is used in a reaction mixture for converting a C-terminal α-hydroxyglycine-containing peptide into the corresponding C-terminal amidated peptide, the use of the above-mentioned co-operative factors are unnecessary and the reaction is preferably carried out at a pH value of about 5 to about 6 at a reaction temperature of about 30° C. to about 40° C.

Though the quantity of PHL enzyme used in the reaction varies depending on the substrate peptide concentration, etc., it is in the range of about 1,000 to about 20,000 units/ml and more preferable from about 5,000 to about 18,000 units/ml (units as defined hereinbefore). Though the reaction temperature varies depending on concentration of substrate peptide and quantity of enzyme, etc., it is usually from about 10 minutes to about 2 days.

In any of the above-mentioned methods, the PHL enzyme used may be a purified enzyme, a partially purified enzyme having been purified to various extents or a crude enzyme. Further, the purified enzyme, partially purified enzyme or crude enzyme may be immobilized by conventional means for immobilization of enzyme such as carrier combination method, crosslinking method, inclusion method and the like, and thereafter put to use.

After the reaction, the C-terminally amidated peptide is recovered and purified. For this purpose, conventional means for recovery and purification of said C-terminally amidated peptide may be adopted directly, e.g. chromatography such as HPLC.

The following examples serve to illustrate the invention, however, they are in no way intended to restrict it.

EXAMPLES

EXAMPLE 1

Purification and Characterization of the PHL Enzyme from *Xenopus laevis* Skin

Frog skin is peeled off from an adult body of *X. laevis*, frozen on dry ice, pulverized with a hammer and homogenized with 50 mM Tris-Cl buffer (pH 7.5) containing 100 μM phenylmethylsulfonyl fluoride (PMSF) by means of a Polytron homogenizer. The homogenate thus obtained is centrifuged, and the supernatant is fractionated by ammonium sulfate precipitation. Thus, after slowly adding ammonium sulfate so that its final concentration reached 25% saturation, the mixture is centrifuged to remove the precipitate. Further, ammonium sulfate is additionally added to the supernatant so that its final concentration reached 55% saturation. The resulting precipitate is collected by centrifugation and re-dissolved into 20 mM bis-Tris-Cl buffer (pH 6.0) containing 100 μM PMSF. This fraction is further fractionated by means of DEAE-Sepharose CL-6B column (manufactured by Pharmacia Co.) (50×250 mm). Thus, after equilibrating the DEAE column in a 20 mM bis-Tris-Cl buffer (pH 6.0) containing 100 μM PMSF, the ammonium sulfate-precipitated fraction is applied thereto. The non-adsorbed components are thoroughly washed away and the adsorbed components are fractionated according to a linear gradient of 0–300 mM NaCl.

In the fractions obtained during DEAE chromatography, activity of the PHL enzyme is measured as follows:

2 mM of benzoylhydroxyglycine is added to a solution containing PHL and 100 mM MES (2-(N-morpholino)-ethanesulfonic acid) (pH 5.2). The mixture is incubated at 37° C. for 30 minutes. Then perchloric acid is added to the reaction mixture to stop the reaction. The mixture is centrifuged and the product in the supernatant is determined by HPLC using Hipore RP-318 (4.6×260 mm; manufactured by Bio-Rad Co.) as a column and 0.1% TFA/12% CH$_3$CN as an eluting solvent system. A quantity of enzyme forming 1 pico mole of amidated product per one minute under the above-mentioned conditions was defined as "one unit".

The activity of PHL is noticeable as two peaks. The main peak is recovered, dialyzed against 50 mM Tris-Cl buffer containing 100 μM PMSF (pH 8.0), and applied to a Mono Q column (HR 16/10, manufactured by Pharmacia Co.) having been equilibrated with the same buffer as above.

After thoroughly washing away the non-adsorbed matter, the adsorbed matter is fractionated by a linear gradient of 0–300 mM NaCl. Fractions exhibiting the activity of this enzyme are concentrated by using Centricon 10 by Amincon Co., and further purified by molecular sieve column chromatography. The molecular sieve column chromatography is carried out by the use of in-series connected two Superose 12 (HR 10/30, manufactured by Pharmacia Co.) columns, and 50 mM potassium phosphats buffer (pH 7.0) containing 150 mM NaCl is used as the solvent.

Among the eluates, the fractions exhibiting peaks of the activity of PHL are analyzed by SDS-polyacrylamide gel electrophoresis. The enzyme has a molecular weight of about 37 KDa, as measured by SDS-polyacrylamide gel electrophoresis using, as standards of molecular weight, phospholipase (molecular weight 97 KDa), bovine serum albumin (66 KDa), ovalbumin (45 KDa), glyceraldehyde-3-phosphate dehydrogenase (36 KDa), carbonic anhydrase (31 KDa) and soybean trypsin inhibitor (22 KDa).

In order to identify PHL additionally, it is fractionated with Mono Q column (HR 5/5, manufactured by Pharmacia Co.) The fraction exhibiting the activity of this enzyme obtained by Superose 12 column chromatography is recovered, 10 times diluted with 50 mM bis-Tris-Cl buffer (pH 6.0), and loaded onto a Mono Q column having previously been equilibrated with the same buffer as above. By a 0–300 mM NaCl linear gradient, the activity of this enzyme is recovered as a single peak. In SDS-polyacrylamide gel electrophoresis, too, a single band having a molecular weight of ca 37 KDa is observed.

Thus, 14 micrograms of a purified enzyme sample is obtained from 55 g of the skin of *Xenopus laevis* at a recovery rate of 3%, at a purification rate of about 1,400 fold.

The enzyme is further characterized by determining optimum working pH, optimum working temperature, stability to pH and stability to temperature. The results are as follows:

Optimum working pH: When the enzyme is reacted upon 2 mM of substrate at 37° C. for 30 minutes in acetic acid/sodium acetate buffer (pH 3.6 and 4.6), MES-Na buffer (pH 5.4 and 6.5) and Tris-Cl buffer (pH 7.5 and 8.5) (all 125 mM), its optimum working pH is about 5.4.

Stability to pH: When PHL is allowed to stand at 4° C. for 24 hours in Tris-Cl buffer (pH 7.5, 8.0 and 8.5) and glycine-Na buffer (pH 9.0 and 9.5) both 250 mM and thereafter reacted upon 2 mM of substrate at 37° C. for 30 minutes in MES-Na substrate (pH 5.2), it exhibited the highest stability at pH 8.5.

Optimum working temperature: When the PHL enzyme is reacted upon 2 mM of substrate at 30° C., 37° C. and 42° for 30 minutes in 100 mM MES-Na buffer (pH 5.2), the enzyme exhibited the highest activity at 37° C., though it exhibited a comparable activity at 30° C. and 42° C., too.

Stability to temperature: When the enzyme is left standing at 37° C. for 83 hours, it lost its activity at pH 7.0 almost completely. However, in the presence of 25% of glycerol or ethylene glycol, it retained about 85% of activity under the same conditions as above. At pH 8.5, about 100% of its activity is retained in the presence of 25% glycerol or ethylene glycol.

Using about 50 pmoles of the enzyme purified above and by means of automatic gas phase amino acid sequencer (Applied Biosynthesis; Model 470A), amino acid sequence of the N-terminus is determined. Further, about 500 pmoles of the enzyme is digested with trypsine. The digested product is separated by reverse phase liquid chromatography (column: Chemocosorb 3μ $C_{18}$-H, 8×75 mm, Chemco; elution: linear gradient by 0-60% acetonitrile in 0.1% trifluoroacetic acid) to obtain 34 kinds of peptide fragments. Amino acid sequences of 32 fragments among the 34 fragments are determined in the same manner as above. The sequences of the fragments correspond to amino acid sequences encoded by the DNA sequence with SEQ ID No. 1 depicted in the sequence listing.

EXAMPLE 2

Cloning and Sequencing of cDNA Coding for *Xenopus laevis* PHL

From the skin of two heads of *Xenopus laevis*, total RNA is extracted by the guanidine thioisocyanate method. From the total RNA, poly(A)RNA is prepared in a purified form by the use of oligo(dT)-latex (Takara Shuzo). Using 5 micrograms of the poly(A)RNA, a double strand cDNA is prepared according to the method of Gubler, U.: Gene, 25, 263–269 (1983). After linking EcoR I linker thereto, the cDNA is linked to the EcoR I site of phage λgt 10, and an in vitro packaging reaction is carried out. Thus, a cDNA library of about $2.5 \times 10^3$ clones is obtained per one nanogram of poly-(A)RNA.

Screening of the library is carried out by the two step method.

The comparison of the amino acid sequence of the PHL from *X. laevis* skin determined in Example 1 with the amino acid sequence of the PAM enzyme AE-II from *X. laevis* skin presumed from the nucleotide sequence of the cDNA published in Ohsuye, K. et al., Biochem. Biophys. Res. Commun. 150, 1275–1281 (1988) shows that both enzymes share sections with homologous sequences.

Thus, in the present case, it is also possible to use a restriction fragment of an AE-II cDNA in order to prescreen the library for clones carrying PHL DNA. Therefore, in the first step for screening out the cDNA coding for PHL, a restriction fragment of the cDNA encoding for AE-II is used as a probe. Thus, a cDNA encoding for AE-II obtained according to the method mentioned in Ohsuye et al., Biochem. Biophys. Res. Commun. 150, 1275–1281 (1988) is digested with a restriction enzyme Xba I to obtain a 814 bp fragment of Xba I (1191)-Xba I(2004), and the latter DNA fragment is labelled with [α-$^{32}$P] dCTP by means of Random Primed DNA Labeling Kit (Boehringer-Mannheim Co.) and used as a probe. The probe is named AE-II-Xba. About $2.5 \times 10^5$ recombinant phages taken from the cDNA library are transferred onto a nylon filter and hybridized with the probe AE-II-Xba at 37° C. for 16 hours in a solution containing 50% formamide, 5×Denhardt's solution (1×Denhardt's solution: 0.2% BSA fraction V, 0.2% polyvinylpyrrolidone, 0.2% Ficoll 400), 6×SSPE (SSPE: 150 mM NaCl, 10 mM NaH$_2$-PO$_4$H$_2$O, 1 mM EDTA, pH adjusted to 7.4), 0.1% SDS and 100 micrograms/ml of denatured salmon sperm DNA. The filter is washed with 1% SDS and 2×SSC (SSC: 150 mM NaCl, 15 mM Na$_3$ citrate 2H$_2$O, pH adjusted to 7.0) at 68° C. three times all for 30 minutes. About $2.5 \times 10^5$ plaques are screened in the above-mentioned manner to obtain 13 positive clones, from which a cDNA coding for PHL is screened out in the following manner.

First, the inserted DNA fragment of the positive clone is directly amplified from a phage DNA obtained from a plaque on the plate by the use of λgt 10 primers (Takara Shuzo) according to the PCR method of Saiki, R. K. et al.: Science, 239, 487–491 (1988). Each of the DNA fragments thus obtained is examined on the possibility of cleavage using restriction enzyme, EcoR V and Kpn I. Clones of AE-II type have an EcoR V-cleavable site at position 1770. On the other hand, clones of PHL type have no corresponding EcoR V-cleavable site but have a Kpn I-Cleavable site at position 1788. As the result, it is revealed that, among the 13 positive clones, 4 are of PHL and 8 of AE-II type. A clone having the longest cDNA chain expectedly coding for PHL is named AE-III-101/λgt 10. Then, in order to obtain a further longer cDNA having a complete length, a 0.5 kb EcoR I/BamH I fragment located in the 5' side of the inserted cDNA of the clone AE-III-101/λgt 10 is prepared, and it is labelled with [α-$^{32}$P] dCTP similarly to the above probe and used as the second probe. This probe is named AE-III-Bam and has the sequence corresponding to that extending from position 745 up to 1275 of the sequence with the SEQ ID No. 1. Using this probe AE-III-Bam and the above-mentioned probe AE-II-Xba, cDNA consisting of $2.5 \times 10^6$ recombinant phages is screened to obtain 15 positive clones hybridizing with both probes in the same manner as the above. They are analyzed in the same manner as in the first screening to reveal that, of the 15 positive clones, 5 positive clones are of PHL type and 8 are of AE-II type. From them, a clone having the longest cDNA expectedly coding for PHL is screened out and named AE-III-202/λgt 10.

DNA sequences of the cDNA parts of the clone AE-III-202/λgt 10 obtained in Example 2 is determined in the following manner.

Phage DNA of AE-III-202/λgt 10 is prepared by ultracentrifugation (Grossberger, D., Nucl. Acids Res. 15; 6737 (1987)) and digested with EcoR I, the two types of DNA fragments containing cDNA are subcloned into Bluescript II vector (Stratagene) to obtain plasmid pAE-III-202-1 and pAE-III-202-2. These plasmids are digested with various restriction enzymes to obtain DNA fragments. They are subcloned using vectors M13mp18, M13mp19, pUC 118 and pUC 119, and DNA sequences are determined according to the dideoxy method. The total sequence thus determined is shown in the sequence listing under SEQ ID No. 1. The sequence of the cDNA insert of AE-III-101/λgt 10 is determined accordingly. It corresponds to the whole region starting at the nucleotide position 745 and ending at the 3' terminus of the sequence with SEQ ID No. 1. The DNA sequence of the insert of plasmid pAE-III-202-1 extends from nucleotide position 1 to 1891, that of the insert of plasmid pAE-III-202-2 from 1891 to 3383.

Plasmid pAE-III-202-4 is prepared by digesting plasmid pAE-III-202-1 with Pst I, removing small fragments, ligating the large DNA fragment, cutting the plasmid thus obtained with EcoR I, and ligating it with the EcoR I cDNA fragment isolated from pAE-III-202-2. The DNA sequence of the insert of pAE-III-202-4 is identical with that shown in the sequence listing under SEQ ID No. 1.

EXAMPLE 3

Expression of AE-III cDNA by Using Baculovirus Expression Vector System (BEVS)

3.1. Construction of expression vector pVL-AE-III

A PstI/EcoRI DNA fragment containing the DNA sequence extending from position 1 up to 1891 of the sequence with SEQ ID No. 1 is prepared from the AE-III cDNA clone pAE-III-202-1. The fragment is inserted into the baculovirus transfer vector pVL1392 (Invitrogen Corp.) digested with PstI and EcoRI. The resulting plasmid DNA is then digested with SmaI and EcoRI. On the other hand, the AE-III cDNA clone, pAE-III-202-2, is digested with AccI to remove a short DNA fragment and both ends of the longer fragment are bluntend with DNA polymerase I. The linear DNA fragment thus obtained is self-ligated. The resulting plasmid pVL-PE contains the sequence extending from position 1891 up to 2310 of the sequence with SEQ ID No. 1. It is digested with HindIII, blunt ended and then digested with EcoRI. The EcoRI-HindIII(blunt) DNA fragment containing the EcoRI(1891)-AccI(2310) part of cDNA clone of AE-III is isolated and inserted into the SmaI and EcoRI digested plasmid described above containing the PstI(1)-EcoRI(1891) fragment (ciphers in brackets refer to the positions in SEQ ID No. 1). The pVL-AE-III plasmid vector thus obtained carries the PstI(1)-AccI(2310) part of the AE-III cDNA. *E. coli* HB101 is used for all cloning steps performed in Example 3.1 and also hereinafter in 3.2.

3.2. Construction of expression vector pVL-PHL pVL-PE described in Example 3.1. is digested with XbaI and blunt ended. Then, pVL-AE-III obtained in Example 3.1. is digested with BstEII (1117), blunt ended and then digested with SphI. The BstEII(blunt)-SphI fragment containing the BstEII(1117)-AccI(2310) part of AE-III cDNA is ligated to the XbaI(blunt) fragment containing the PstI(1)-XbaI(211) part of AE-III cDNA and the pVL1392 vector part of pVL-AE-III. Thus obtained pVL-PHL vector does not contain the PHM domain of AE-III encoded by DNA sequences between base positions 212 and 1117, but only the PHL domain.

3.3. Insect cell culture

*Spodoptera frugiperda* (Sf9) cells (ATCC, CRL1711) are maintained as monolayer culture in TNM-FH medium supplemented with 10% fetal bovine serum and antibiotics. After infection with the recombinant virus, the medium is replaced by EX-CELL 400 (J-R. Scientific), a serum-free medium. Wild-type Baculovirus and transfer vector pVL1392 are obtained from Invitrogen Corp., San Diego, Calif., USA.

3.4. Construction of recombinant baculovirus

Sf9 cells are transfected with mixtures of wild-type AcNPV DNA and pVL-AE-III or pVL-PHL leading to recombinant viruses AcAE-III and AcPHL, respectively. The recombinant viruses are isolated and purified by combination of cDNA hybridization and plaque assay, then used to infect monolayers of Sf9 cells for subsequent experiments.

3.5. Cell extraction and enzyme assay

The insect cells infected with wild-type AcNPV or recombinant AcAE-III or AcPHL virus (cellular fraction) and medium (medium fraction) are collected at 4 days post infection. The cells are resuspended in 50 mM Tris-Cl, 0.5% Lubrol PX (pH 7.5). After mixing for 15 min at 4° C., the supernatants are collected and used as cellular fractions. PHM activity in the medium and cellular fractions is determined as described in Example 1 with a slight modification: The standard reaction mixture used is changed to 200 mM TES-Na (pH 6.4), 2 mM L-ascorbate, 10 mM KI, 1 $\mu$M $CuSO_4$, 2 mM N-ethylmaleimide, 20 $\mu$M N-dansyl-Tyr-Phe-Gly, 100 $\mu$g/ml catalase. PHL activity is measured as production of N-dansyl-Tyr-Phe-$NH_2$ from the α-hydroxylated precursor N-dansyl-Tyr-Phe-Gly(OH) which is isolated as described above in Example 1. The reaction mixture is adjusted to 200 mM TES-Na (pH 6.4) and 20 $\mu$m N-dansyl-Tyr-Phe-Gly(OH). After the incubation at 30° C. for 15 min, the reaction is stopped by adding EDTA to a final concentration of 50 mM. The results (in "units" as defined hereinbefore) are given in the following Table 1:

TABLE 1

PHM and PHL activities (units/ml) in the medium or the cells from insect cell cultures

| insect cell culture | | PHM activity | PHL activity |
|---|---|---|---|
| AcNPV | Medium | 0 | 903 |
| (Wild-type) | Cell | 0 | 188 |
| AcAE-III | Medium | 16881 | 19833 |
| | Cell | 8016 | 6815 |
| AcPHL | Medium | 0 | 24612 |
| | Cell | 0 | 3592 |

EXAMPLE 4

Preparation of C-terminal Hydroxyglycine-extended Human Calcitonin by Means of the "Amidating Enzyme" PAM To 0.2M MES-Na buffer solution (pH 6.0) containing 2 mM of L-ascorbic acid, 0.1 mg/ml of catalase and 10 mM of potassium iodide is added 26 mg of C-terminal glycine-extended human calcitonin (a peptide having an additional glycine residue on the C-terminus of 32-proline of human calcitonin, hCT-Gly). Further, 0.6 mg of purified peptidylglycine α-hydroxylating monooxygenase (identical with the peptidylglycine α-amidating monooxygenase PAM mentioned in British Patent Application No. 9006354.6) is added thereto. After incubating the mixture at 30° C. for 5 hours, it is treated with SEPPAK C-18 (Waters), freeze-dried, and then purified by HPLC. Thus, 20.5 mg of the dried product is dissolved into 0.6 ml of 90% acetic acid and purified with Bio-Rad Hi Pore RP 304 (10×250 mm) column. Elution is carried out by linear concentration gradient of 19% to 23% acetonitrile in 10 mM ammonium formate (pH 4). The eluted fractions are united and freeze-dried to obtain 14.6 mg of C-terminal hydroxyglycine-extended human calcitonin (hCT-GlyOH). The HPLC is carried out with Bio-Rad Hi Pore RP 304 (4.6×250 mm) column by linear gradient of 8% to 50% acetonitrile in 10 mM ammonium formate (pH 4.0), and optical absorbance is measured at 210 nm. The result demonstrated that the powder obtained herein is pure.

Analysis of the Human Hydroxyglycine-extended Calcitonin

Amino acid sequence: Using 30 micrograms of the peptide obtained in Example 4, Edman decomposition is carried out by means of a gas phase sequencer, and the resulting PTH-amino acid is identified by means of PTH analyzer to determine the amino acid sequence. The result indicates that the peptide obtained in the above-mentioned examples completely coincides with the amino acid residues in positions 1 to 32 of human calcitonin.

$^1$H-NMR-Spectrum: Five milligrams of the peptide obtained in Example 3 is dissolved into water (90% light water, 10% heavy water, pH 3.2). Its 500 MHz $^1$H-NMR is measured, and the results are analyzed. The proton signals are assigned according to DQF-COSY (double-quantum-filtered correlated spectroscopy). Asignal assignable to alpha proton of α-hydroxyglycine is observed at about 5.4 ppm. DQF-COSY spectrum (cross zone of alpha proton and NH proton), where cross peaks of alpha proton and amide proton in hydroxyglycine are observed at 5.4 ppm and 8.7 ppm, indicates also that the α-hydroxyglycine is contained in the peptide in a combined form.

Positive ion FAB-MS: Using 20 micrograms of the peptide obtained in the examples, positive ion FAB-MS is measured. As the result, the corresponding protonated molecule is observed at about m/Z=3,490. This satisfies the structure of C-terminal hydroxyglycine-extended human calcitonin.

EXAMPLE 5

Formation of Human Calcitonin from the Human Calcitonin Precursor hCT-Gly

To 50 microliters of 200 mM MES-Na buffer (pH 5.5) containing 0.5 mM (87 micrograms) of human calcitonin precursor (hCT-Gly) having an additional glycine unit on C-terminus of human calcitonin (hCT) as a substrate and further containing 2 mM of ascorbic acid, 0.5 μM CuSO$_4$, 10 mM of KI, 20 micrograms/ml of catalase and 1% of acetonitrile is added either (1) 800 units (about 20 ng) of the purified peptidylhydroxyglycine N-C lyase (PHL) obtained according to Example 1 or of the recombinant PHL obtained as the product of AcPHL in Example 3, (2) 5,700 units (6 micrograms) of purified peptidylglycine α-hydroxylating monooxygenase (PHM) from X. laevis or (3) a combination of 800 units (about 20 ng) of the purified peptidylhydroxyglycine N-C lyase (PHL) obtained according to Example 1 and 5,700 units (6 micrograms) of purified PHM from X. laevis or (4) 800 units of the product of AcAE-III obtained according to Example 3. After reacting the resulting mixture at 30° C. for 50 minutes, the peptide produced in the reaction mixture is separated and detected by the use of HPLC system.

The detection is carried out at a wavelength of 210 nm. As the column, Hipore RP304 (4.6×250 mm, manufactured by Bio-Rad Co.) is used. As eluting solvent system, 10 mM ammonium formate (pH 4.0) containing 26% of acetonitrile is used. At a flow rate of 1.0 ml/min., the substrate (hCT-Gly) and the α-hydroxylated intermediate (hCT-GlyOH) are slightly separated from each other and detected at 10.9 minutes and 10.2 minutes after the start, respectively. The amidated product, i.e. human CT, is detected at about 13.5 minutes after the start. When only the purified PHL enzyme is used, the peak detected in the HPLC does not shift and no change takes place on substrate hCT-Gly, while when only the purified PHM from X. laevis is used the peak slightly shifts and the substrate CT-Gly is converted to intermediate hCT-GlyOH. When either the AcAE-III product or the combination of the PHM and PHL enzymes is used, the peak shifts to a great extent, demonstrating that the substrate hCT-Gly is converted to human calcitonin hCT.

EXAMPLE 6

Formation of Human Calcitonin from the Human Calcitonin Precursor hCT-GlyOH

One thousand units (ca. 25 ng) of the purified enzyme of the present invention (peptidylhydroxyglycine N-C lyase) are added to 50 microliters of 200 mM MES-Na buffer (pH 6.0) containing as a substrate 0.5 mM (87 micrograms) of the human calcitonin precursor hCT-GlyOH (the peptide prepared in Example 4) in which a α-hydroxyglycine unit is added to C-terminus of human calcitonin (hCT), and the mixture is reacted at 30° C. for one hour. After the reaction, the peptide in the reaction mixture is separated and detected by the use of HPLC system. If the detection of the product is analyzed as above, it is apparent that the purified PHL enzyme uses hCT-GlyOH as a substrate and converts it into amidated hCT.

Deposited Microorganisms

Echerichia coli HB101:pAE-III-202-4 containing plasmid pAE-III-202-4 was deposited as FERM BP-3174 according to the Budapest Treaty with the Fermentation Research Institute, Agency of Industrial Science & Technology, 1-3, Higashi 1 Chome, Tsukuba-shi, Ibaragi-ken 305, Japan, on Nov. 26, 1990.

---

Claimed is:

1. A recombinant DNA molecule selected from the group of molecules consisting of hybrid vectors and manufactured DNA molecules which can be used for preparation of hybrid vectors, said recombinant DNA molecule comprising a DNA sequence encoding the polypeptide from *Xenopus laevis* with peptidylhydroxyglycine N-C lyase (PHL) activity which polypeptide catalyzes the following reaction

wherein R represents a peptide residue, and GlyOH represents an α-hydroxyglycine residue linked to the C-terminus of said peptide R by an amide bond, said DNA sequence consisting essentially of the nucleotide sequence extending from position 1177 to 2148 of the sequence with SEQ ID No. 1.

2. A DNA molecule according to claim 1 consisting essentially of the DNA sequence with the SEQ ID No. 1.

3. A DNA molecule according to claim 1 which is a hybrid vector.

4. A DNA molecule according to claim 3 which is the vector pAE-III-202-4 (FERM BP-3174), pVL-AE-III, AcAE-III, pVL-PHL or AcPHL.

5. A DNA molecule according to claim 3 which is an expression vector.

6. A transformed host comprising a recombinant DNA molecule according to claim 1.

7. A transformed host according to claim 6 which is *E. coli* HB101 transformed with pAE-III-202-4 (FERM BP-3174).

8. A method for the preparation of a polypeptide from *Xenopus laevis* with PHL activity comprising transformed host according to claim 6 and isolating the expressed product.

9. A method for the preparation of a recombinant DNA molecule according to claim 1 comprising:
   a) isolating genomic DNA from suitable cells, and selecting the desired DNA; or
   b) isolating mRNA from suitable cells, selecting the desired mRNA, preparing single-stranded cDNA complementary to that mRNA, then preparing double-stranded cDNA therefrom; or
   c) isolating cDNA from a cDNA library and selecting the desired cDNA; or
   d) incorporating the double-stranded DNA of step a, b, or c into a hybrid vector, transforming suitable host cells with the obtained hybrid vector, selecting transformed host cells which contain the desired DNA from untransformed host cells and multiplicating the transformed host cells, and isolating the desired DNA; or e) excising a DNA fragment encoding a polypeptide with PHL activity from a hybrid vector of the invention, optionally together with flanking sequences derived from the vector or linker sequences; or f) synthesizing a DNA molecule encoding a polypeptide with PHL activity in vitro by chemical synthesis.

10. A method for the preparation of a transformed host according to claim 6 comprising treatment of a suitable host cell under transforming conditions with a recombinant DNA molecule of claim 1, optionally together with a selection marker gene, and selecting the transformants.

11. A method for the preparation of a recombinant DNA molecule according to claim 9 comprising:

a) isolating genomic DNA from suitable cells, and selecting the desired DNA using a DNA probe or a suitable expression system and screening for expression of the desired polypeptide; or b) isolating mRNA from suitable cells, selecting the desired mRNA by hybridization with a DNA probe or by expression in a suitable expression system and screening for expression of the desired polypeptide, preparing single-stranded cDNA complementary to that mRNA, then preparing double-stranded cDNA therefrom; or c) isolating cDNA from a cDNA library and selecting the desired cDNA using a DNA probe or a suitable expression system and screening for expression of the desired polypeptide; or d) incorporating the double-stranded DNA of step a, b, or c into a hybrid vector, transforming suitable host cells with the obtained hybrid vector, selecting transformed host cells which contain the desired DNA from untransformed host cells and multiplicating the transformed host cells, and isolating the desired DNA; or e) excising a DNA fragment encoding a polypeptide with PHL activity from a hybrid vector of the invention, optionally together with flanking sequences derived from the vector or linker sequences; or f) synthesizing a DNA molecule encoding a polypeptide with PHL activity in vitro by chemical synthesis.

* * * * *